(12) United States Patent
Norris et al.

(10) Patent No.: US 8,740,795 B2
(45) Date of Patent: Jun. 3, 2014

(54) REFLECTIVE NON-CONTACT OCULAR PULSE ANALYZER FOR CLINICAL DIAGNOSIS OF EYE AND CEREBROVASCULAR DISEASE

(76) Inventors: John Lawrence Norris, Santa Rosa, CA (US); Robert W Allison, Jr., Rocklin, CA (US)

( * ) Notice: Subject to any disclaimer, the term of this patent is extended or adjusted under 35 U.S.C. 154(b) by 1349 days.

(21) Appl. No.: 12/077,778

(22) Filed: Mar. 21, 2008

(65) Prior Publication Data

US 2008/0242965 A1    Oct. 2, 2008

Related U.S. Application Data

(60) Provisional application No. 60/920,209, filed on Mar. 26, 2007.

(51) Int. Cl.
*A61B 3/16*    (2006.01)

(52) U.S. Cl.
CPC .. *A61B 3/165* (2013.01); *A61B 3/16* (2013.01)
USPC .............................. 600/399; 600/398; 600/402

(58) Field of Classification Search
CPC ...... A61B 3/1015; A61B 3/102; A61B 3/107; A61B 3/113; A61B 3/14; A61B 3/16; A61B 3/165
USPC ......... 600/398, 399, 400, 401, 402, 403, 404, 600/405, 406
See application file for complete search history.

(56) References Cited

U.S. PATENT DOCUMENTS

| | | | |
|---|---|---|---|
| 2,519,681 A | 8/1950 | Mages | |
| 3,049,001 A | 8/1962 | Mackay et al. | |
| 3,070,087 A | 12/1962 | Sittel | |
| 3,181,351 A | 5/1965 | Stauffer | |
| 5,101,113 A * | 3/1992 | Hirleman et al. | 250/574 |
| 5,148,807 A * | 9/1992 | Hsu | 600/402 |
| 5,474,066 A * | 12/1995 | Grolman | 600/398 |
| 5,810,005 A * | 9/1998 | Dublin et al. | 600/398 |
| 5,857,969 A | 1/1999 | Massey et al. | |
| 5,954,645 A * | 9/1999 | Luce | 600/401 |
| 6,033,075 A * | 3/2000 | Fujieda et al. | 351/212 |

(Continued)

FOREIGN PATENT DOCUMENTS

RU    2103906 C1 * 12/1992 ............... A61B 5/02

OTHER PUBLICATIONS

RU 2103906 Cl. English Abstract. Derwent. 2009.*

(Continued)

*Primary Examiner* — Max Hindenburg
*Assistant Examiner* — Adam Eiseman

(57) ABSTRACT

An instrument has been designed to study the pulsatile motion of the eye by analysis of a beam of light reflected from the corneal surface. A laser light beam probe of small spot size and low divergence strikes the cornea apex and the reflected movement is recorded by a sensor. Analysis of the beam movement reveals the energy in the eye pulse without the necessity of physically touching the eye. The value of the intraocular pressure is determined from the calculated power spectrum. The sensitivity, accuracy and efficiency of the light beam makes possible studying both eyes concurrently and comparison of the pulse parameters of onset, amplitude and duration reveals any delay in circulation to an eye.

16 Claims, 9 Drawing Sheets

(56) References Cited

U.S. PATENT DOCUMENTS

| | | | |
|---|---|---|---|
| 6,110,110 | A | 8/2000 | Dublin et al. |
| 6,673,014 | B2 * | 1/2004 | Badehi et al. ................. 600/398 |
| 6,776,756 | B2 | 8/2004 | Feldon et al. |
| 7,201,720 | B2 | 4/2007 | Cuzzani et al. |
| 2002/0049373 | A1 * | 4/2002 | Miwa ............................ 600/401 |
| 2004/0039298 | A1 * | 2/2004 | Abreu ........................... 600/558 |
| 2005/0030473 | A1 * | 2/2005 | Fahrenkrug et al. .......... 351/200 |

OTHER PUBLICATIONS

Kinsner, W and Y Yan. "An Eye Model for Ocular Pulse Analysis." IEEE Engineering in Medicine and Biology Society 11th Annual International Conference. 1989.*

R. N.Weinreb, et al (editors), Intraocular Pressure, 4th Global AIGS Consensus Meeting on Intraocular Pressure, pp. 17 to 58, Kugler Publications, 2007, Amsterdam.

* cited by examiner

REFLECTIVE NON-CONTACT OCULAR PULSE ANALYZER FOR CLINICAL DIAGNOSIS OF EYE AND CEREBROVASCULAR DISEASE

CROSS-REFERENCE TO RELATED APPLICATIONS

This application is related to U.S. Provisional Patent Application Ser. No. 60/920,209 filed on Mar. 26, 2007, the entire disclosure of which is incorporated by reference as if set forth in its entirety herein.

FIELD OF THE INVENTION

The present invention relates generally to ophthalmic clinical screening for the detection of eye and cerebrovascular disease by means of non-contact measurement of the ocular pulse amplitude of a subject's eyes.

BACKGROUND OF THE INVENTION

Determination of the intraocular pressure (IOP) is a component of the standard complete eye examination, a necessary test in the diagnosis and management of glaucoma and an indicator of underlying cerebrovascular diseases. A direct measure of the IOP requires surgically opening the eye and placing a device within it. This is not clinically useful on a large scale. Clinically, indirect methods are required to determine the IOP. The instruments used for this determination are called tonometers. Tonometers evaluate the IOP by seeing how much force it takes to distort the eye and inferring what intraocular pressure is required to resist the applied force, and declaring that to be the IOP.

The force is applied to the eye by a plunger, an illuminated prism, a blast of air, a pneumatic pressure probe or piezoelectric crystals. All of these methods suffer from multiple problems. First, distorting the shape of the eye changes the pressure in the eye reducing the accuracy of the test. Second, all of these instruments have a large mechanical component introducing friction into the measurement. The damping effect of friction decreases the sensitivity of the test. Third, the force required for a tonometer to indent or flatten the eye surface in measuring the IOP is large compared to the energy contained within the ocular pulse wave. Therefore, the information carried in the ocular pulse wave and created in the eye following each heart beat remains hidden. Fourth, the lack of ability to produce detailed ocular pulse wave measurements eliminates the opportunity to test both eyes concurrently and to compare this data between the eyes. Fifth, applying force to the eye subjects the cornea to trauma.

SUMMARY OF THE INVENTION

Our invention relates generally to ophthalmic clinical screening for the detection of eye and cerebrovascular disease by a non-contact measurement of the ocular pulse amplitude waveform The invention, an ocular pulse analyzer, probes the eye with a light beam and evaluates the eye's expansile response to an ocular pulse by analyzing movement of the reflected light beam. Valuable information about the ocular pulse is recorded in real time. The eye is not touched. The eye is not distorted. There is no friction interfering with the data and there is no trauma to the eye. The time of onset of the ocular pulse after the heart beat is easily measured. The amplitude of the ocular pulse, the duration of the ocular pulse and the shape of the ocular pulse are recorded to be compared with normal values for each parameter. Since both eyes are tested concurrently, they are compared with each other.

An embodiment of the ocular pulse analyzer consists of a pulsed laser diode followed by a laser beam expander/collimator and a laser beam shaper which form a low divergence small spot incident beam that strikes the corneal surface at a large incident angle. The reflected beam emerges at an equal and opposite incident angle, striking the analyzer CCD array forming a pixelated image of the beam spot. During a single ocular pulse up to 128 points are obtained by calculating the center-of-gravity of each reflected beam spot profile. The distance of each data point from the CCD array systolic reference point is proportional to the distance the front eye surface has moved. The collection of these points defines the ocular pulse amplitude waveform for each heart pulse. Sensors are used to generate triggers that pulse the laser and synchronize the analyzer control and data acquisition. Fast Fourier Transforms (FFT) are used to analyze the data producing both the ocular pulse waveform and its power spectrum. The zero-frequency power spectrum area is a measure of the energy in the mean intraocular pressure (IOP). Non-zero frequency power spectra areas measure energy that may be related to pressure changes during the ocular pulse and may be indicators of eye disease. Left-right eye data comparison allows rapid detection of eye and cerebrovascular disease. Two of these optical analyzers may be mounted so that both of the subject's eyes can be examined simultaneously.

BRIEF DESCRIPTION OF THE FIGURES

Understanding of the present invention will be facilitated by consideration of the following detailed description of an embodiment of the present invention taken in conjunction with the accompanying drawings, in which like numerals refer to like parts and in which.

DETAILED DESCRIPTION OF THE INVENTION

It is to be understood that the figures and the descriptions of the present invention have been simplified to illustrate elements that are relevant for a clear understanding of the present invention Several standard optical elements and other components are used to expand and collimate and form the laser beam and to control and process it. Those of ordinary skill in the arts will recognize that these and other optical elements and/or steps are well known in the art, but because they do not facilitate a better understanding of the present invention, a discussion of such elements and steps is not provided herein. The disclosure herein is directed to all such variations to such elements and methods known to those skilled in the art.

Figure 1:
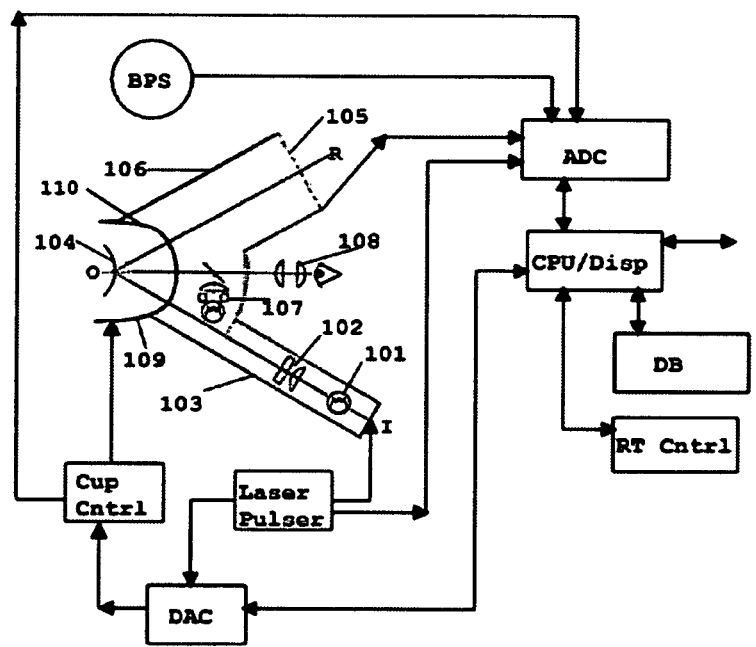
FIG. 1 illustrates a functional block diagram of the device according to an aspect of the present invention.

FIG. 1 is a block diagram of an embodiment of the ocular pulse analyzer. A solid state laser 101 produces a pulsed axially symmetric Gaussian beam of 670 nm wavelength and 1 milliwatt power, which is injected along the incident-beam-line 10 into the beam forming optics module 102, which forms a small diameter low divergence exit beam of up to 500 micrometers diameter and less than 1.0 milliradians divergence, which strikes the apex of the cornea O at a 65 to 75 degree angle with respect to the eye visual axis. The incident beam is reflected onto the reflected-beam-line OR at an angle of −65 to −75 degrees where it strikes a CCD array 105 forming a pixelated image of the reflected beam spot. The motion of the beam spot pixelated image on CCD array 105 is proportional to the movement of the eye front surface 104 as it responds to the ocular pulse. The eye orbit cup 109 is a compliant cup that forms an air tight seal on the eye orbit so that the equilibrium pressure at the eye front surface can be varied which allows parametric studies of the eye. Cup 109 also is the interface to the patient's face. The optics target module 107 projects an infinity image of an eye fixation target on which the patient focuses his vision thus minimizing random eye movement. Accessory optics port module 108 which allows access for the external calibration of the optics system. Both the fixation module 107 and the accessory optics port module 108 are aligned to the apparatus centerline. The ocular pulse analyzer beam forming optics are contained in beam tube 103, and the reflected beam components are contained in beam tube 106. The fixation module 107, the observation module 108 and the eye orbit cup 109 are attached to an instrument stand 110.

The laser pulser is synchronized to the heart pulse by delayed triggers derived from the blood pulse sensors BPS. During each heart pulse up to 128 pixelated beam spot widths are digitized by the analog-to-digital-converter ADC and processed to provide measurements of the eye surface movement. The computer/display module CPU/Disp system processes these data providing the operator with the IOP and other parameters. These data are stored in the patient data base DB. The CPU/Disp receives the pulse and timing data and sends control data to the DAC which then controls the Laser Pulser and the cup control module Cup Cntrl. By using the real time control module RTCntrl the operator controls the measurement and data processing parameters.

Figure 2:
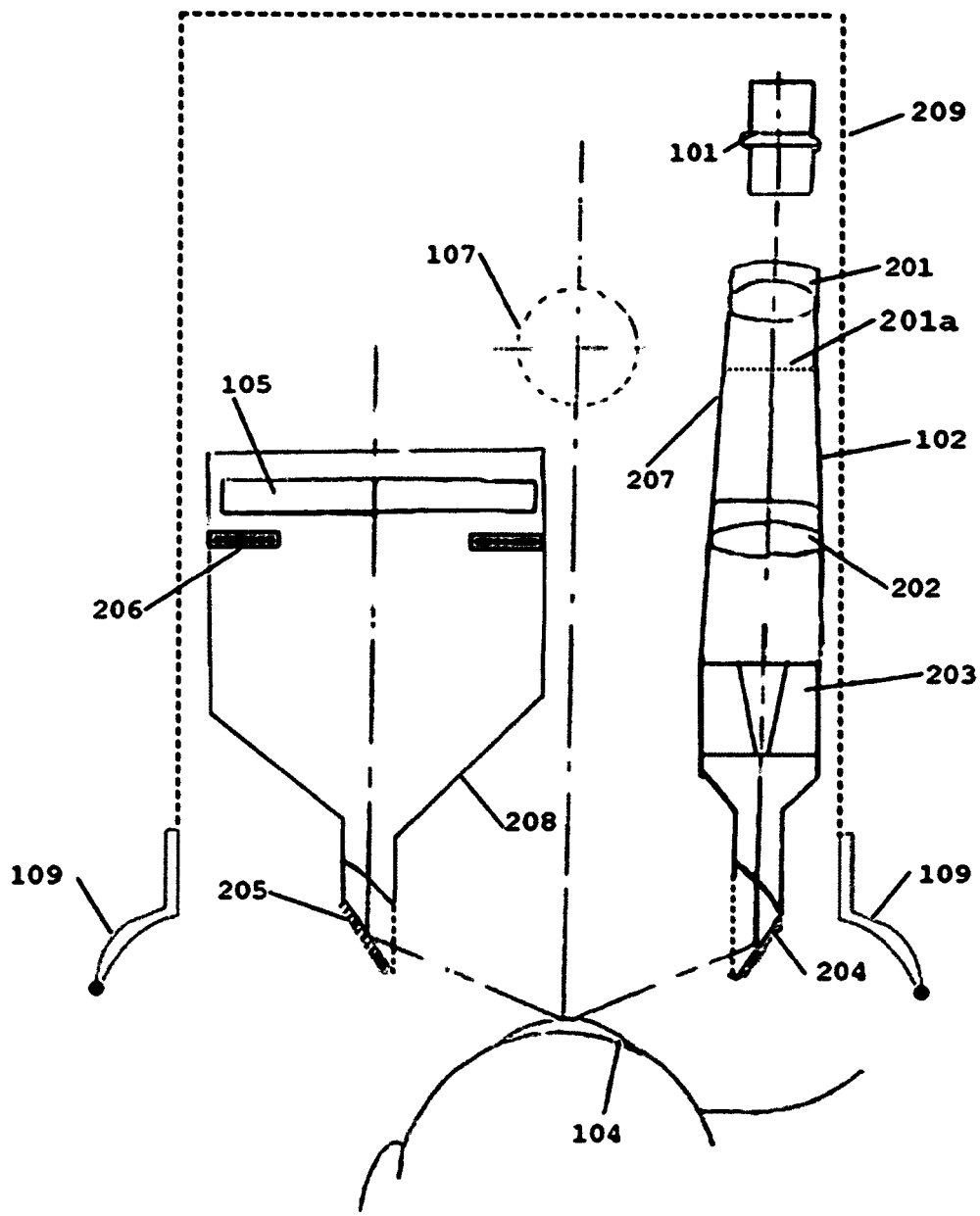
FIG. 2 illustrates a diagram of a folded optical system for the left eye for measuring the movement of the eye front surface during the ocular pulse for the apparatus of FIG. 1.

FIG. 2 illustrates an embodiment of a compact left eye optic head 200 with mirror folded beam lines allowing high angle light reflection on the cornea. The incident laser beam from laser 101 is transformed by the beam forming module 102 which is comprised of a 2.5× inverted Kepler's telescope that expands and collimates the beam. Kepler's Telescope consists of a diffraction limited entrance lens 201 such as an infinity corrected 5× microscope objective of 36 mm focal length and numerical aperture 0.1, which forms a beam waist of about 14 micrometers diameter at image plane 201a, followed by an exit lens 202 such as a 90 mm focal length doublet located about one focal length from plane 201a which forms a well collimated exit beam of at most 10 mm diameter and a total beam divergence of less than 0.5 mrad at the entrance of beam shaper, collimator and dump module 203 which attenuates and collimates the beam using apertures of decreasing diameter. At the beam shaper, collimator and dump module 203 exit the beam has a diameter no larger than 500 micrometers, a divergence of less than 1.0 mrad and a power of less than 1 microwatt. The beam then strikes turning mirror 204, which reflects the incident beam so that it strikes the cornea at an angle of from 65 to 75 degrees to the normal of the eye where it is reflected at an equal and opposite angle striking turning mirror 205, which reflects the beam onto the normal to CCD array 105. The beam then passes through the quadrature error detectors 206 which detect reflected beam centering and out of range reflected beam pulses, finally impinging onto CCD array 105 which forms a pixelated image of the reflected beam spot. To provide noise and stray light shielding; the beam forming module 102 is mounted in beam tube 207, the reflected beam tube components 206 and 105 in beam tube 208 and the compact optic head 200 in instrument case 209, which also mounts the orbit cup 109 and mounts the fixation module 107 and the accessory optics port module 108. As may be understood by those possessing an ordinary skill in the pertinent arts instrument case 209 may be mounted on a standard slit lamp bench or other ophthalmic examination stand.

Figure 3:
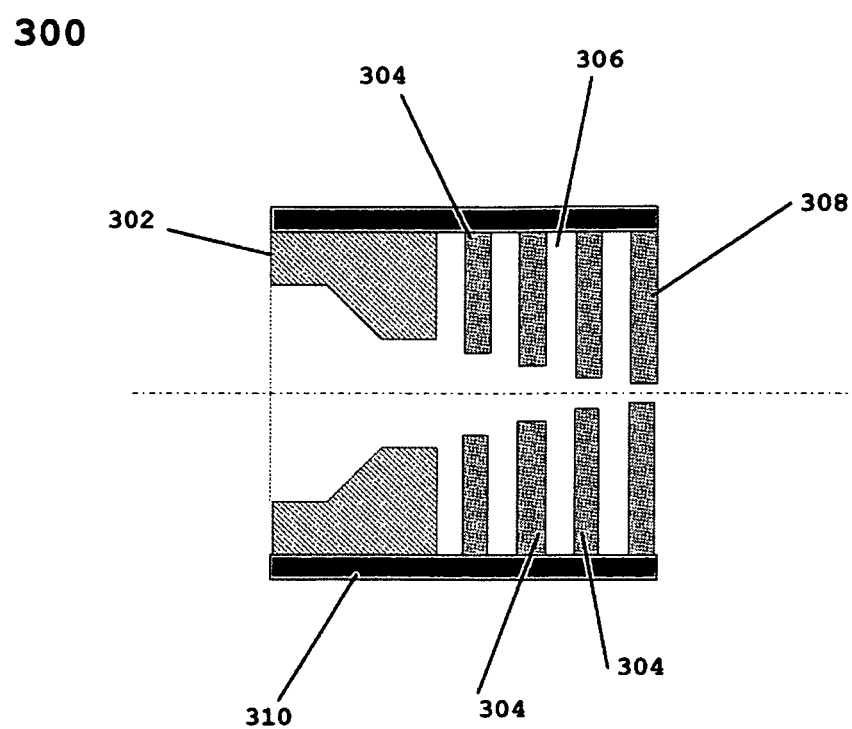
FIG. 3 is a cross section of the light beam shaping, collimator, and beam dump module 203 of FIG. 2 for the apparatus of FIG. 1.

FIG. 3 details an embodiment of a beam shaper, collimator and beam dump module 203 which simultaneously forms the probe beam that is required for observing the unperturbed movement of the eye front surface. The expanded laser beam enters module 203 through an aperture in wall 302 where the laser beam diameter is reduced by striking the walls which are conical and may be made of graphite, the beam then passes through four alternating radial light traps 306 and four decreasing apertures 304 further reducing the beam diameter, divergence and power. Light traps 306 collect large angle light rays, and scattered rays from the wall by multiple reflections in the radial traps further reducing stray light. After passing through a beam defining exit aperture 308 the beam power may be reduced by a factor greater than 1000, may have a reduction in beam divergence to less than 1 milliradian and a diameter of less than 500 micrometers. As may be understood by those possessing an ordinary skill in the pertinent arts the apertures may be produced by laser or other machining means and may be coated with an optically absorbent coating by sputtering or other means. The internal parts may be assembled with spacers into a stack that is self aligning.

Figure 4:
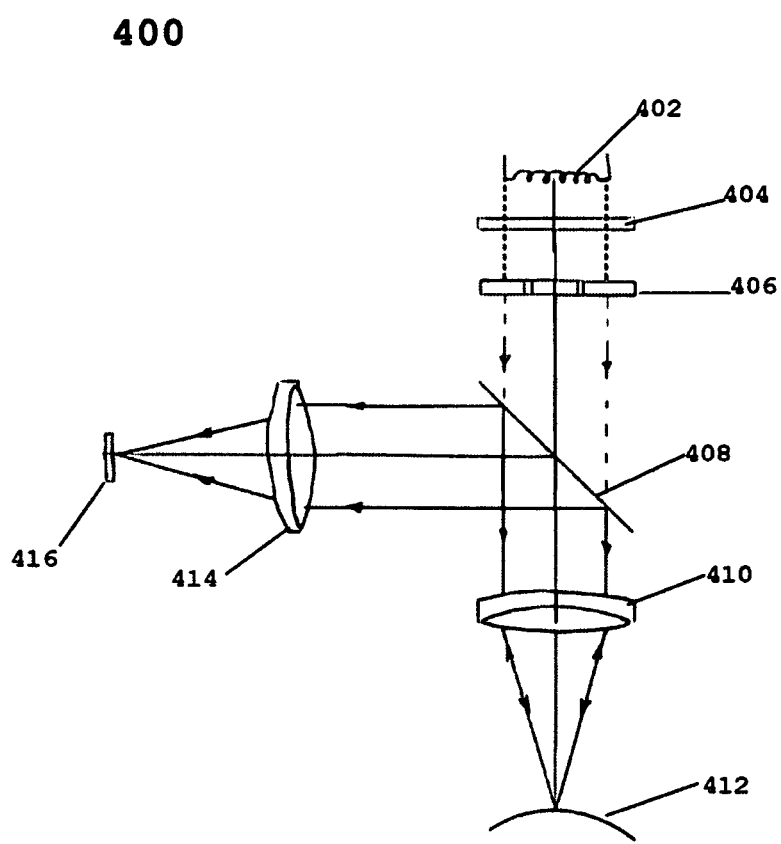
FIG. 4 is a layout of the patient and operator optics 107 and 108 of FIG. 2 for the apparatus of FIG. 1.

FIG. 4 illustrates the eye fixation module 107 and accessory optics port module 108. An incandescent light source 402 illuminates a ground glass 404, which illuminates an optical fixation target 406. Light from target 406 passes through beam splitter 408, onto lens 410 which forms an image of the fixation target at infinity, which the patient fixes his eye on, minimizing random eye motion. Light from the eye surface 412 is reflected 90 degrees by beam splitter 408 onto lens 414 which forms an image of eye surface 412 on at the exit of the accessory optics port 416, which provides access for external calibration of the optics system.

Figure 5:
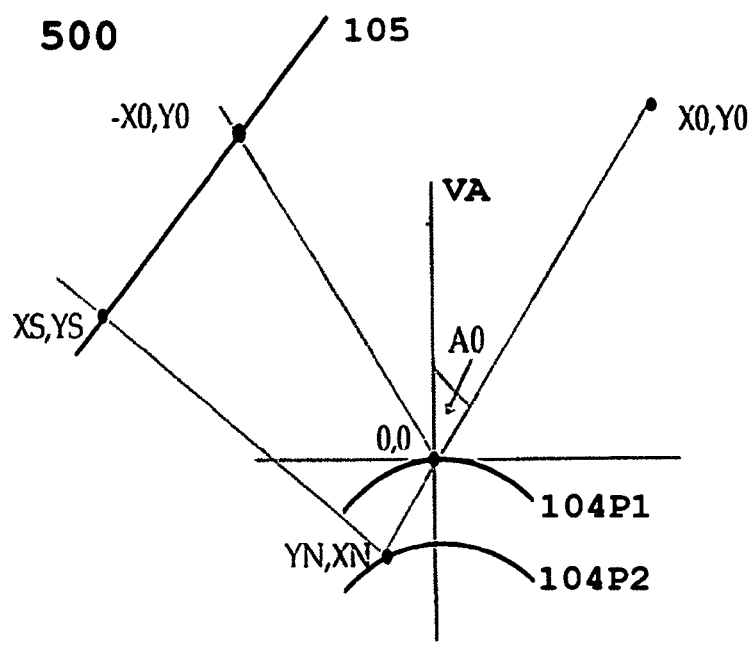
FIG. 5 illustrates how the light beam responds to the movement of the eye front surface in response to the ocular pulse.

FIG. 5 shows a geometric model of how the reflective head functions. Initially the optic head is aligned to the eye surface at $t_0$ the time of the systolic ocular pulse, when the eye surface 104 has moved to its maximum outward extent 104P1. At this time the optics projects the apertured beam spot image onto the corneal apex (0,0) and reflects it onto the CCD array 105 which forms a pixelated spot image that is collected by the data processing system. As the ocular pulse amplitude reduces, the eye surface 104 moves inward. The projection of the incident beam is not changed, but the angle of incidence to the perturbed eye surface is changed. The reflected light centroid is shifted on the CCD array 105, and the relative position of the beam on the detector increases. A similar situation occurs when the ocular pulse pressure is raised, except that the reflected light shift moves in the opposite direction. The curvature of the cornea and the change in the location of the eye surface normal with respect to the incident beam provide a 50 times magnification of the eye surface movement at an incident angle of 75 degrees with an equal incident and reflected beam drift length. The measurement of the eye surface motion can be explained from the single ray trace deflection diagram given in FIG. 5 which shows two positions of the eye surface 104 during a single ocular pulse. At time $t_0$ the eye surface 104 is at (0,0) where the incident beam strikes the cornea. As the ocular pulse amplitude decreases the eye front surface 104 moves radially inward along the eye normal axis VA, moving to the second eye surface 104 position 104P2. To measure this movement we place a small diameter, low divergence light source at the point (X0, Y0) aligned so that the center of the output beam intersects the initial eye surface 104P1 at (0,0). The angle A0 between the input ray and the eye surface normal axis is the angle of incidence of the input beam. Physically the laws of reflection apply and the incident light ray is reflected along line (0,0)-(−X0, Y0) where it strikes the detector at the pixel located at the point (−X0, Y0) where the beam intensity profile is collected and the profile center of gravity calculated. At time $(t_0+\delta t)$ the eye surface 104 moves towards the eye center along the eye normal until it reaches the second eye surface position 104P2 where the incident beam intersects the surface at the point (XN, YN) and is reflected to the array detector at point (XS, YS) along a new normal and a different angle of incidence where another beam profile is collected and a center of gravity calculated. The distance between the two reflected beam detector profiles is proportional to the displacement of the two eye surface locations.

Figure 6:
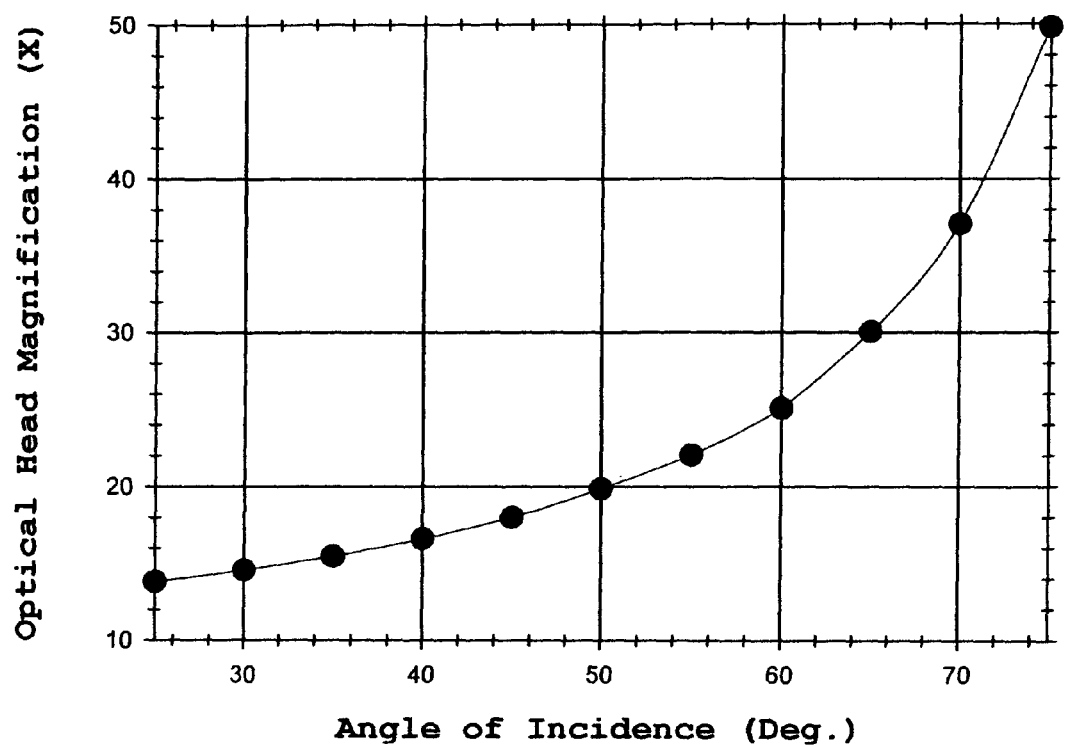
FIG. 6 is a plot of the light beam optical magnification vs. the incident angle of the input laser beam illustrating the variation of magnification.
Figure 7:
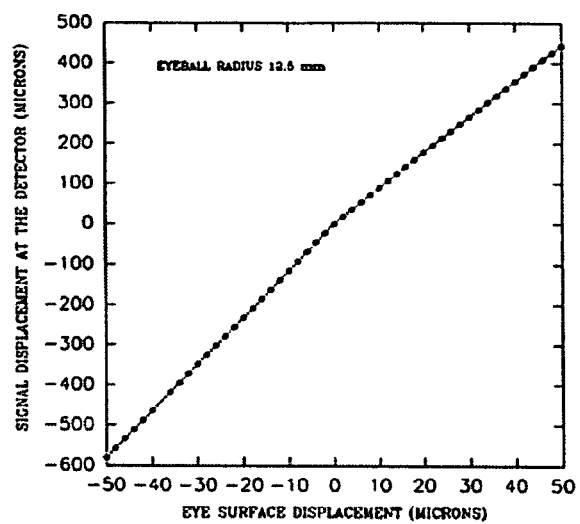
FIG. 7 is a plot of the displacement of the light beam vs. the displacement of the eye surface in response to the ocular pulse.
Figure 8:
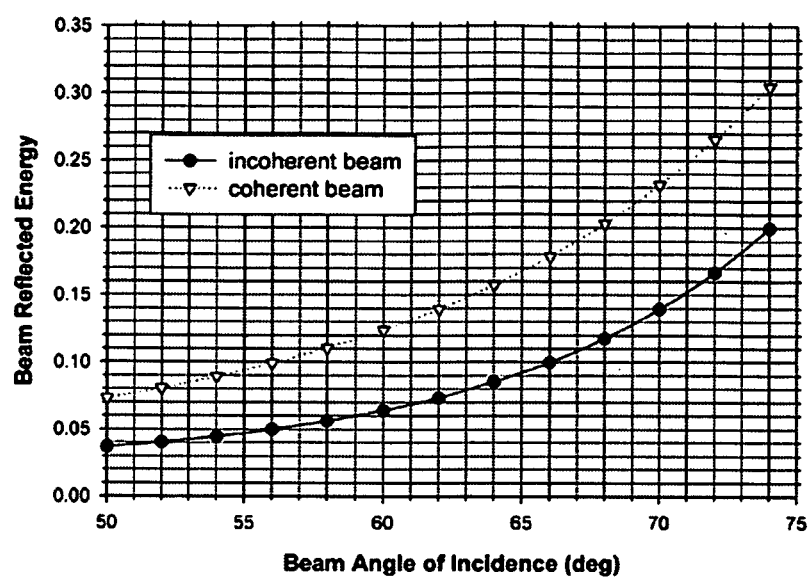
FIG. 8 is a plot of the reflected light beam energy at the optical detector as a function of the light beam incident angle.

FIGS. 6 through 8 show the dependence of magnification on the angle of incidence, the pixelated signal displacement as a function of the eye surface motion and the fraction of beam reflected power as a function of the angle of incidence. FIG. 6 shows the dependence of the reflective head sensor magnification on the angle of incidence A0. There is a strong dependence of magnification on the angle of incidence. Facial obstructions limit the maximum angle of incidence to 75 degrees or less with a useful range of 65 to 75 degrees corresponding to a magnification range of about 30 to 50 times. FIG. 7 is a plot of the pixelated beam spot image displacement as a function of the eye surface movement for a 12.5 mm radius spheroidal eye ball with an 8.5 mm corneal radius and an incident beam angle of 75 degrees and a magnification of 50×. Note that a 50 micrometer movement of the eye surface as it responds to the ocular pulse causes a 450 micrometer displacement on CCD array 105. FIG. 8 shows the dependence of the energy reflected from the eye as a function of the beam incident angle for both incoherent and coherent light beams. The model results show that a coherent beam reflects more beam energy than an incoherent beam. FIG. 8 also shows that for an incident angle of 75 degrees that the reflectivity of the coherent beam is 32% and that of the incoherent beam is 20%. The coherent beam reflected power is 1.6 times as high as the incoherent beam. The refracted beam powers are 68% and 80%. Since we wish to lower the beam refracted into the eye an incident angle of 75 degrees is desirable.

Figure 9:
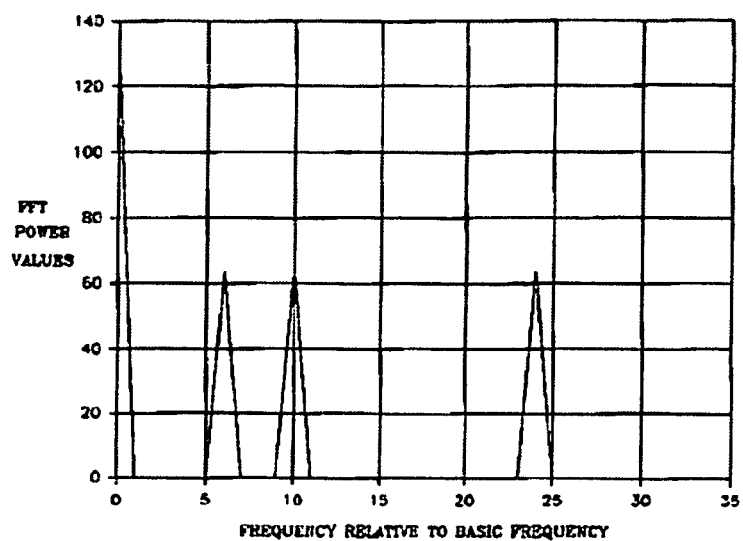
FIG. 9 is a plot of a simulated power spectrum illustrating the IOP as the zero frequency component with three higher frequency components.

FIG. 9 is a plot of a FFT algorithm power spectrum calculated using a simulated ocular pulse amplitude wave train. Note that the plot shows four spectral power peaks the zero frequency power intensity plus three higher frequency components. The area under the zero frequency peak directly gives the mean energy in the eye ball that generates the IOP. The higher frequency spectral components are natural oscillations of the eye generated as the ocular pulse ebbs and flows without external drive or instrumental effects. Variations in these components may give data on the health of the eye and the cerebrovascular system.

Those of ordinary skill in the art will recognize that many modifications and variations of the present invention may be implemented without departing from the spirit or scope of the invention. Thus, it is intended that the present invention cover the modification and variations of this invention provided they come within the scope of the appended claims and their equivalents.

What is claimed is:

1. A method for evaluating eye disease by measuring eye surface movement during an ocular pulse, said method comprising:
   identifying a blood pulse by sphygmomanometer on an arm, electrocardiography or ultrasonography;
   using a laser light source to form a coherent gaussian, sub-millimeter diameter, low divergence probe beam that strikes the central cornea of the eye at a high angle of incidence;
   using a processor synchronizing the beam with a blood pulse selected with a sphygmometer, electrocardiogram or ultrasonogram and record eye front surface movement;
   magnifying a received reflection from the cornea of the beam that strikes a CCD camera sensor array;
   calculating with a processor from the received beam reflected a plurality of parameters, including at least two from the group consisting of an ocular pulse amplitude waveform, a power spectra, a zero frequency amplitude of power spectrum, and non-zero frequency amplitudes, wherein the zero frequency amplitude of the power spectrum is a measure of energy in a mean intraocular pressure, and non-zero amplitudes are a measure of pressure changes during the ocular pulse that are indicative of eye disease.

2. The method of claim 1 using the heart pulse identified by arm sphygmomanometer, electrocardiogram or ultrasonography, wherein said forming includes striking the cornea of the eye.

3. The method of claim 1 using the heart pulse found by arm sphygmometer, electrocardiogram or ultrasonography, wherein the high angle of incidence is in the range of 65 to 75 degrees with respect to the visual axis.

4. The method of claim 3, wherein the high angle of incidence is 65 degrees.

5. The method of claim 3, wherein the high angle of incidence is 70 degrees.

6. The method of claim 3, wherein the high angle of incidence is 75 degrees.

7. The method of claim 1, wherein the sub-millimeter diameter is a beam diameter less than 500 micrometers.

8. The method of claim 1, wherein the low divergence probe beam has a divergence of approximately 1 mrad.

9. The method of claim 1, wherein the power of the probe beam is approximately 1 microwatt.

10. The method of claim 1, further comprising monitoring a blood pressure sensor correspondent to the eye.

11. The method of claim 1, where the spectral energy of higher frequency components of the eye are used to determine the cerebrovascular behavior of the eye and the mean pressure of the eye.

12. The method of claim 1, further comprising a forming and synchronizing a second probe beam to test a second eye concurrently.

13. The method of claim 12, further comprising magnifying a received reflection of the second beam and calculating in a processor a plurality of output parameters for said second beam.

14. The method of claim 13, wherein said processor calculated output parameters for said second beam are compared to the beam parameters to provide indicia of artery ailments.

15. The method of claim 14, wherein said artery ailments include at least one of the carotid artery and a chest artery.

16. The method of claim 1, wherein said processor generated output parameters provide indicia of at least one of glaucoma and ocular artery occlusion.

* * * * *